(12) United States Patent
Mann

(10) Patent No.: US 9,930,889 B2
(45) Date of Patent: Apr. 3, 2018

(54) SYNERGISTIC WEED CONTROL FROM APPLICATIONS OF PENOXSULAM AND MEFENACET

(71) Applicant: Dow AgroSciences LLC, Indianapolis, IN (US)

(72) Inventor: Richard K. Mann, Franklin, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/102,009

(22) Filed: Dec. 10, 2013

(65) Prior Publication Data

US 2014/0179531 A1    Jun. 26, 2014

Related U.S. Application Data

(60) Provisional application No. 61/736,273, filed on Dec. 12, 2012.

(51) Int. Cl.

| *A01N 43/78* | (2006.01) |
|---|---|
| *A01N 43/90* | (2006.01) |
| *A01N 41/06* | (2006.01) |
| *A01N 43/653* | (2006.01) |
| *A01N 37/22* | (2006.01) |
| *A01N 43/713* | (2006.01) |

(52) U.S. Cl.
CPC ............. *A01N 43/78* (2013.01); *A01N 37/22* (2013.01); *A01N 41/06* (2013.01); *A01N 43/653* (2013.01); *A01N 43/713* (2013.01); *A01N 43/90* (2013.01)

(58) Field of Classification Search
CPC ........ A01N 43/78; A01N 43/90; A01N 41/06; A01N 43/653; A01N 37/22; A01N 43/713
See application file for complete search history.

(56) References Cited

U.S. PATENT DOCUMENTS

| 5,858,924 | A | 1/1999 | Ehr et al. |
|---|---|---|---|
| 7,314,849 | B2 | 1/2008 | Balko et al. |
| 7,432,227 | B2 | 10/2008 | Balko et al. |
| 8,071,508 | B2 | 12/2011 | Keenan et al. |
| 2002/0045549 | A1* | 4/2002 | Kruger et al. ................. 504/211 |
| 2002/0055435 | A1 | 5/2002 | Baltruschat et al. |
| 2006/0167018 | A1 | 7/2006 | Zagar et al. |
| 2008/0153704 | A1 | 6/2008 | Yamaji et al. |
| 2010/0016158 | A1 | 1/2010 | Kilian et al. |
| 2010/0099564 | A1 | 4/2010 | Hacker et al. |
| 2010/0190794 | A1 | 7/2010 | Hupe et al. |
| 2010/0279864 | A1 | 11/2010 | Mann et al. |
| 2011/0059847 | A1 | 3/2011 | Endo et al. |
| 2011/0092367 | A1 | 4/2011 | Griveau et al. |
| 2011/0190134 | A1 | 8/2011 | Jousseaume et al. |
| 2011/0190135 | A1 | 8/2011 | Mann et al. |
| 2011/0190136 | A1 | 8/2011 | Hufnagl et al. |
| 2012/0071320 | A1 | 3/2012 | Atkinson et al. |
| 2012/0142532 | A1 | 6/2012 | Wright et al. |
| 2012/0238449 | A1 | 9/2012 | Mann |
| 2012/0284812 | A1 | 11/2012 | Mankin et al. |
| 2014/0031214 | A1 | 1/2014 | Yerkes et al. |

FOREIGN PATENT DOCUMENTS

| CN | 1514686 | 7/2004 | |
|---|---|---|---|
| CN | 1761395 | 4/2006 | |
| CN | 101128115 | 2/2008 | |
| CN | 101647450 | 2/2010 | |
| CN | 101647450 A * | 2/2010 | ............. A01N 43/90 |
| CN | 103798255 | 5/2014 | |
| CN | 103875686 | 6/2014 | |
| EP | 1313369 | 6/2005 | |
| JP | 2001233718 | 8/2001 | |
| JP | 2009013114 A | 1/2009 | |
| JP | 2012171928 A | 9/2012 | |
| WO | 2002078442 | 10/2002 | |
| WO | 2004080171 | 9/2004 | |
| WO | 2006086640 | 8/2006 | |
| WO | WO 2007/032532 A2 * | 3/2007 | |
| WO | WO 2011/097187 A2 * | 8/2011 | ............. A01N 37/26 |

OTHER PUBLICATIONS

Penoxsulam data sheert (obtained onlince via www.alanwood.net, on May 9, 2017).*
Mefenacet data sheert (obtained onlince via www.alanwood.net, on May 9, 2017).*
Farm Chemical International, Crop Protection Database, "Mefenacet," available at http://www.farmchemicalsinternational.com/crop-protection-database/#/product/detail/251820/ (accessed on May 28, 2014).
Farm Chemical International, Crop Protection Database, "Penoxsulam," available at http://www.farmchemicalsinternational.com/crop-protection-database/#/product/detail/424174/ (accessed on May 27, 2014).
Tomlin, C. D. S., Ed., The Pesticide Manual: A World Compendium, "Mefenacet," 15th ed., BCPC: Alton, 2009, pp. 722-723.
Tomlin, C. D. S., Ed., The Pesticide Manual: A World Compendium, "Penoxsulam," 15th ed., BCPC: Alton, 2009, pp. 874-875.

(Continued)

*Primary Examiner* — Mina Haghighatian
*Assistant Examiner* — Mei Ping Chui
(74) *Attorney, Agent, or Firm* — Michael R. Asam; Meunier Carlin & Curfman LLC

(57) ABSTRACT

Disclosed herein are herbicidal compositions comprising a synergistically herbicidal effective amount of (a) penoxsulam, or an agriculturally acceptable salt thereof, and (b) mefenacet, or an agriculturally acceptable salt thereof. Also disclosed herein are methods of controlling undesirable vegetation in rice, which comprise applying to vegetation or an area adjacent the vegetation or applying to soil or water to prevent the emergence or growth of vegetation (a) penoxsulam, or an agriculturally acceptable salt thereof, and (b) mefenacet, or an agriculturally acceptable salt thereof, wherein (a) and (b) are each added in an amount sufficient to produce a synergistic herbicidal effect.

9 Claims, No Drawings

(56) References Cited

OTHER PUBLICATIONS

International Search Report and Written Opinion dated Mar. 25, 2014, in related International Patent Application No. PCT/US2013/074134.

Disclosed anonymously 462055: "2-(2,2-difluoroethoxy)-6-trifluoromethyl1-N-(5,8-dimethoxy[1,2,4]triazolo[1,5-c]pyrimidin-2-y1)benzenesulfonamide and its use as a herbicide in mixtures." Research Disclosure, Oct. 2002, pp. 1832-1833.

Office Action issued in related application No. JP2015-547471 dated Jun. 27, 2017.

Office Action issued in related Russian application No. 2015127775 dated Aug. 9, 2017.

* cited by examiner

SYNERGISTIC WEED CONTROL FROM APPLICATIONS OF PENOXSULAM AND MEFENACET

CROSS REFERENCE TO RELATED APPLICATIONS

This application claims the benefit of U.S. Provisional Patent Application Ser. No. 61/736,273 filed Dec. 12, 2012, the disclosure of which is expressly incorporated herein by reference.

FIELD OF THE DISCLOSURE

The present disclosure relates to herbicidal compositions comprising a synergistically herbicidal effective amount of (a) penoxsulam or an agriculturally acceptable salt thereof and (b) mefenacet or an agriculturally acceptable salt thereof. The present disclosure also relates to methods for controlling undesirable vegetation in rice.

BACKGROUND

Many recurring problems in agriculture involve controlling growth of undesirable vegetation that can, for instance, inhibit crop growth. To help control undesirable vegetation, researchers have produced a variety of chemicals and chemical formulations effective in controlling such unwanted growth. However, a continuing need exists for new compositions and methods to control growth of undesirable vegetation.

SUMMARY OF THE DISCLOSURE

Herbicides of many types have been disclosed in the literature and a number are in commercial use. In some cases, herbicidal active ingredients have been found more effective in combination than when applied individually and this is referred to as "synergy" or "synergism." The present disclosure is based on the discovery that (a) penoxsulam or an agriculturally acceptable salt thereof and (b) mefenacet or an agriculturally acceptable salt thereof display a synergistic herbicidal effect when applied in combination.

Accordingly, the present disclosure relates to herbicidal compositions comprising a synergistically herbicidal effective amount of (a) penoxsulam, or an agriculturally acceptable salt thereof, and (b) mefenacet, or an agriculturally acceptable salt thereof. The weight ratio of (a) to (b) can be from 1:400 to less than 1:30 (e.g., from 1:80 to less than 1:30, or from 1:56 to less than 1:30). In some embodiments, the composition further comprises an additional pesticide (e.g., cyhalofop, bensulfuron, bentazon, benzobicyclon, bromobutide, fenoxaprop, halosulfuron, metamifop, metazosulfuron, metsulfuron, profoxydim, pyrazosulfuron, triafamone, agriculturally acceptable salts or esters thereof, or combinations thereof). In some embodiments, the composition further comprises a herbicidal safener, an agriculturally acceptable adjuvant or carrier, or a combination thereof.

The present disclosure also relates to methods of controlling undesirable vegetation in rice, which comprise applying to vegetation or an area adjacent the vegetation or applying to soil or water to prevent the emergence or growth of vegetation (a) penoxsulam or an agriculturally acceptable salt thereof and (b) mefenacet or an agriculturally acceptable salt thereof, wherein (a) and (b) are each applied in an amount sufficient to produce a synergistic herbicidal effect. In some embodiments, (a) and (b) are applied simultaneously. In some embodiments, (a) and (b) are applied pre-emergence to the undesirable vegetation. The undesirable vegetation can be, for example, a broadleaf weed, a sedge weed, a grassy weed, or combinations thereof. In some embodiments, the undesirable vegetation includes barnyard grass, kuro-guwai, common false pimpernel, dwarf arrowhead, and combinations thereof. In certain embodiments, the undesirable vegetation can be controlled in flooded rice.

In some embodiments, (a) is applied in an amount of from 5-75 grams of active ingredient per hectare (g ai/ha) (e.g., from 18-70 g ai/ha). In some embodiments, (b) is applied in an amount of from 250-2000 g ai/ha (e.g., from 500-1000 g ai/ha). Penoxsulam (a) and mefenacet (b) can be applied in a weight ratio of from 1:400 to 1:3.3 (e.g., from 1:80 to 1:7, from 1:56 to 1:7, from 1:80 to 1:14, or from 1:56 to 1:14). In certain embodiments, (a) to (b) can be applied in a weight ratio of from 1:400 to less than 1:30 (e.g., from 1:80 to less than 1:30, or from 1:56 to less than 1:30).

The description below sets forth details of one or more embodiments of the present disclosure. Other features, objects, and advantages will be apparent from the description and from the claims.

DETAILED DESCRIPTION

The present disclosure relates to herbicidal compositions comprising a synergistically herbicidal effective amount of (a) penoxsulam or an agriculturally acceptable salt thereof and (b) mefenacet or an agriculturally acceptable salt thereof. The present disclosure also relates to methods for controlling undesirable vegetation in rice.

The term "herbicide," as used herein, means an active ingredient that kills, controls, or otherwise adversely modifies the growth of vegetation. A "herbicidally effective amount" is an amount of an active ingredient that causes a "herbicidal effect," i.e., an adversely modifying effect and includes deviations from, for instance, natural development, killing, regulation, desiccation, and retardation. The terms "plants" and "vegetation" can include, for instance, germinant seeds, emerging seedlings, and established vegetation.

Penoxsulam

Compositions and methods of the present disclosure can include penoxsulam (i.e., 2-(2,2-difluoroethoxy)-N-(5,8-dimethoxy[1,2,4]triazolo[1,5-c]pyrimidin-2-yl)-6-trifluoromethyl)benzenesulfonamide) or an agriculturally acceptable salt thereof. Penoxsulam, shown below, is a triazolopyrimidine sulfonamide herbicide that provides broad-spectrum control of many annual, biannual, and perennial weeds. Penoxsulam, as well as methods of preparing penoxsulam, are known in the art. See, for example, U.S. Pat. No. 5,858,924 to Loughner, et al.

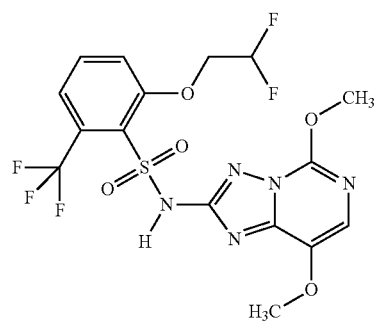 [SMILES: COc1cnc(OC)n2nc(NS(=O)(=O)c3c(OCC(F)F)cccc3C(F)(F)F)nc12]

In some embodiments, penoxsulam can be provided as an agriculturally acceptable salt of penoxsulam. Exemplary agriculturally acceptable salts of penoxsulam include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy- $C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl) ammonium salts, olamine salts, and diglycolamine salts.

Penoxsulam can be used, for example, to control grass, broadleaf and sedge weeds in rice, to control broadleaf weeds in cereal crops, and to control grass, broadleaf, and sedge weeds in lawns (e.g., residential, industrial, and institutional), golf courses, parks, cemeteries, athletic fields, sod farms, range and pasture, rights-of-way, roadsides, and other crop and non-crop uses. Its herbicidal activity is described in Tomlin, C. D. S., Ed. *The Pesticide Manual: A World Compendium,* 15$^{th}$ ed.; BCPC: Alton, 2009 (hereafter "*The Pesticide Manual*, Fifteenth Edition, 2009"). Penoxsulam is or has been commercially available, for example, from Dow AgroSciences, LLC under the trademarks CLIPPER®, BENGALA®, FENCER®, WIDEATTACK®, SAPPHIRE®, VIPER®, GRASP®, and GRANITE®, and from SePRO Corporation under the trademark GALLEON®.

Penoxsulam or an agriculturally acceptable salt thereof can be applied to vegetation or an area adjacent the vegetation or applied to soil or water to prevent the emergence or growth of vegetation in an amount sufficient to induce a herbicidal effect. In some embodiments, the penoxsulam or agriculturally acceptable salt thereof is applied to vegetation or an area adjacent the vegetation or applied to soil or water to prevent the emergence or growth of vegetation in an amount of 5 grams of active ingredient per hectare (g ai/ha) or greater (e.g., 6 g ai/ha or greater, 7 g ai/ha or greater, 7.5 g ai/ha or greater, 8 g ai/ha or greater, 9 g ai/ha or greater, 10 g ai/ha or greater, 15 g ai/ha or greater, 18 g ai/ha or greater, 20 g ai/ha or greater, 25 g ai/ha or greater, 30 g ai/ha or greater, 35 g ai/ha or greater, 40 g ai/ha or greater, 45 g ai/ha or greater, 50 g ai/ha or greater, 55 g ai/ha or greater, 60 g ai/ha or greater, 65 g ai/ha or greater, or 70 g ai/ha or greater). In some embodiments, the penoxsulam or agriculturally acceptable salt thereof is applied to vegetation or an area adjacent the vegetation or applied to soil or water to prevent the emergence or growth of vegetation in an amount of 75 g ai/ha or less (e.g., 70 g ai/ha or less, 65 g ai/ha or less, 60 g ai/ha or less, 55 g ai/ha or less, 50 g ai/ha or less, 45 g ai/ha or less, 40 g ai/ha or less, 35 g ai/ha or less, 30 g ai/ha or less, 25 g ai/ha or less, 20 g ai/ha or less, 18 g ai/ha or less, 15 g ai/ha or less, 10 g ai/ha or less, 9 g ai/ha or less, 8 g ai/ha or less, 7.5 g ai/ha or less, 7 g ai/ha or less, or 6 g ai/ha or less).

Penoxsulam can be applied to vegetation or an area adjacent the vegetation or applied to soil or water to prevent the emergence or growth of vegetation in an amount ranging from any of the minimum values described above to any of the maximum values described above. In some embodiments, the penoxsulam or agriculturally acceptable salt thereof is applied to vegetation or an area adjacent the vegetation or applied to soil or water to prevent the emergence or growth of vegetation in an amount of from 5-75 g ai/ha (e.g., from 6-70 g ai/ha, from 7.5-65 g ai/ha, from 10-55 g ai/ha, from 12.5-45 g ai/ha, or from 15-35 g ai/ha). In some embodiments, the penoxsulam or agriculturally acceptable salt thereof is applied to vegetation or an area adjacent the vegetation or applied to soil or water to prevent the emergence or growth of vegetation in an amount of from 18-70 g ai/ha.

Mefenacet

Compositions and methods of the present disclosure can include mefenacet or an agriculturally acceptable salt thereof. Mefenacet (i.e., 2-(2-benzothiazolyloxy)-N-methyl-N-phenylacetamide), shown below, is an oxyacetamide herbicide that can be used to control broadleaf weeds in rice. Its herbicidal activity is described in *The Pesticide Manual*, Fifteenth Edition, 2009.

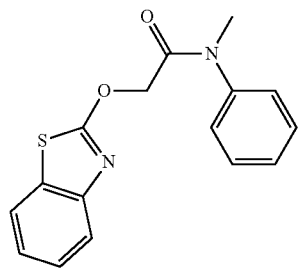 [SMILES: CN(C(=O)COc1nc2ccccc2s1)c1ccccc1]

In some embodiments, mefenacet can be provided as an agriculturally acceptable salt. Exemplary agriculturally acceptable salts of mefenacet include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, and diglycolamine salts.

Mefenacet is or has been commercially available, for example, under the trademarks HINOCHLOA® (by Bayer CropScience), RANCHO® (by Bayer CropScience), and FACE-IT® (by Wangs Crop-Science Co., Ltd.).

The mefenacet or an agriculturally acceptable salt thereof can be used in an amount sufficient to induce a herbicidal effect. In some embodiments, the mefenacet or agriculturally acceptable salt thereof is applied to vegetation or an area adjacent the vegetation or applied to soil or water to prevent the emergence or growth of vegetation in an amount of 250 grams of active ingredient per hectare (g ai/ha) or greater (e.g., 275 g ai/ha or greater, 300 g ai/ha or greater, 325 g ai/ha or greater, 350 g ai/ha or greater, 375 g ai/ha or greater, 400 g ai/ha or greater, 425 g ai/ha or greater, 450 g ai/ha or greater, 475 g ai/ha or greater, 500 g ai/ha or greater, 525 g ai/ha or greater, 550 g ai/ha or greater, 575 g ai/ha or greater, 600 g ai/ha or greater, 625 g ai/ha or greater, 650 g ai/ha or greater, 675 g ai/ha or greater, 700 g ai/ha or greater, 725 g ai/ha or greater, 750 g ai/ha or greater, 775 g ai/ha or greater, 800 g ai/ha or greater, 850 g ai/ha or greater, 900 g ai/ha or greater, 950 g ai/ha or greater, 1000 g ai/ha or greater, 1100 g ai/ha or greater, 1200 g ai/ha or greater, 1250 g ai/ha or greater, 1300 g ai/ha or greater, 1400 g ai/ha or greater, 1500 g ai/ha or greater, 1600 g ai/ha or greater, 1700 g ai/ha or greater, 1750 g ai/ha or greater, 1800 g ai/ha or greater, 1900 g ai/ha or greater, or 2000 g ai/ha or greater). In some embodiments, the mefenacet or agriculturally acceptable salt thereof is applied to vegetation or an area adjacent the vegetation or applied to soil or water to prevent the emergence or growth of vegetation in an amount of 2000 g ai/ha or less (e.g., 1900 g ai/ha or less, 1800 g ai/ha or less, 1750 g ai/ha or less, 1700 g ai/ha or less, 1600 g ai/ha or less, 1500 g ai/ha or less, 1400 g ai/ha or less, 1300 g ai/ha or less, 1250 g ai/ha or less, 1200 g ai/ha or less, 1100 g ai/ha or less, 1000 g ai/ha or less, 950 g ai/ha or less, 900 g ai/ha or less, 850 g ai/ha or less, 800 g ai/ha or less, 775 g ai/ha or less, 750 g ai/ha or less, 725 g ai/ha or less, 700 g ai/ha or less, 675 g ai/ha or less, 650 g ai/ha or less, 625 g ai/ha or less, 600 g ai/ha or less, 575 g ai/ha or less, 550 g ai/ha or less, 525 g ai/ha or less, 500 g ai/ha or less, 475 g ai/ha or less, 450 g ai/ha or less, 425 g ai/ha or less, 400 g ai/ha or less, 375 g ai/ha or less, 350 g ai/ha or less, 325 g ai/ha or less, 300 g ai/ha or less, 275 g ai/ha or less, or 250 g ai/ha or less).

Mefenacet can be applied to vegetation or an area adjacent the vegetation or applied to soil or water to prevent the emergence or growth of vegetation in an amount ranging from any of the minimum values described above to any of the maximum values described above. In some embodiments, the mefenacet or agriculturally acceptable salt thereof is applied to vegetation or an area adjacent the vegetation or applied to soil or water to prevent the emergence or growth of vegetation in an amount of from 250-2000 g ai/ha (e.g., from 300-1750 g ai/ha, from 350-1500 g ai/ha, from 400-1250 g ai/ha, from 450-1000 g ai/ha, from 500-1000 g ai/ha or from 500-750 g ai/ha).

Herbicidal Mixtures or Combinations

The (a) penoxsulam or an agriculturally acceptable salt thereof is mixed with or applied in combination with (b) mefenacet or an agriculturally acceptable salt thereof in an amount sufficient to induce a synergistic herbicidal effect. In some embodiments, (a) and (b) are used in an amount sufficient to induce a synergistic herbicidal effect while still showing good crop compatibility (i.e., their use in crops does not result in increased damage to crops when compared to the individual application of the herbicidal compounds (a) or (b)). As described in the *Herbicide Handbook* of the Weed Science Society of America, Ninth Edition, 2007, p. 429, "'synergism' [is] an interaction of two or more factors such that the effect when combined is greater than the predicted effect based on the response to each factor applied separately." Synergistic in the herbicide context can mean that the use of (a) and (b) as defined above results in an increased weed control effect compared to the weed control effects that are possible with the use of (a) or (b) alone. In some embodiments, the damage or injury to the undesired vegetation caused by the compositions and methods disclosed herein is evaluated using a scale from 0% to 100%, when compared with the untreated control vegetation, wherein 0% indicates no damage to the undesired vegetation and 100% indicates complete destruction of the undesired vegetation. In some embodiments, Colby's formula is applied to determine whether using (a) and (b) in combination shows a synergistic effect: S. R. Colby, *Calculating Synergistic and Antagonistic Responses of Herbicide Combinations*, WEEDS 15, p. 22 (1967)

$$E = X + Y - \frac{X*Y}{100}$$

wherein

X=effect in percent using (a) penoxsulam or an agriculturally acceptable salt thereof at an application rate a;

Y=effect in percent using (b) mefenacet or an agriculturally acceptable salt thereof at an application rate b;

E=expected effect in percent using (a)+(b) at application rates a and b.

In Colby's equation, the value E corresponds to the effect (plant control or injury) that is to be expected if the activity of the individual compounds is additive. If the observed effect is higher than the value E calculated according to the Colby equation, then a synergistic effect is present according to the Colby equation.

In some embodiments, the compositions and methods disclosed herein are synergistic as defined by the Colby equation. In some embodiments, the joint action of penoxsulam or an agriculturally acceptable salt thereof and mefenacet or an agriculturally acceptable salt thereof results in enhanced activity against undesired vegetation (via synergism), even at application rates below those typically used for the pesticide to have a herbicidal effect on its own. In some embodiments, the compositions and methods disclosed herein can, based on the individual components, be used at lower application rates to achieve a herbicidal effect comparable to the effect produced by the individual components at normal application rates. In some embodiments, the compositions and methods disclosed herein provide an accelerated action on undesired vegetation (i.e., they effect damaging of undesired vegetation more quickly compared with application of the individual herbicides).

Provided are compositions and formulations that comprise a weight ratio of (a) penoxsulam or agriculturally acceptable salt thereof to (b) mefenacet or an agriculturally acceptable salt thereof that is sufficient to induce a synergistic herbicidal effect. In some embodiments, the composition or formulation can comprise (a) and (b) in a weight ratio of at least 1:400 (e.g., at least 1:375, at least 1:350, at least 1:325, at least 1:300, at least 1:275, at least 1:250, at least 1:225, at least 1:200, at least 1:175, at least 1:150, at least 1:125, at least 1:100, at least 1:95, at least 1:90, at least 1:85, at least 1:80, at least 1:75, at least 1:70, at least 1:65, at least 1:64, at least 1:63, at least 1:62, at least 1:61, at least 1:60, at least 1:59, at least 1:58, at least 1:57, at least 1:56, at least 1:55, at least 1:54, at least 1:53, at least 1:52, at least 1:51, at least 1:50, at least 1:49, at least 1:48, at least 1:47, at least 1:46, at least 1:45, at least 1:44, at least 1:43, at least 1:42, at least 1:41, at least 1:40, at least 1:39, at least 1:38, at least 1:37, at least 1:36, at least 1:35, at least 1:34, at least 1:33, at least 1:32, at least 1:31, at least 1:30, at least 1:27.5, at least 1:25, at least 1:22.5, at least 1:20, at least 1:17.5, at least 1:15, at least 1:12.5, at least 1:10, at least 1:7.5, at least 1:7, at least 1:6, at least 1:5, or at least 1:4). In some embodiments, the composition or formulation comprises (a) and (b) in a weight ratio that is less than 1:3.3 (e.g., less than 1:4, less than 1:5, less than 1:6, less than 1:7, less than 1:7.5, less than 1:10, less than 1:12.5, less than 1:15, less than 1:17.5, less than 1:20, less than 1:22.5, less than 1:25, less than 1:27.5, less than 1:30, less than 1:31, less than 1:32, less than 1:33, less than 1:34, less than 1:35, less than 1:36, less than 1:37, less than 1:38, less than 1:39, less than 1:40, less than 1:41, less than 1:42, less than 1:43, less than 1:44, less than 1:45, less than 1:46, less than 1:47, less than 1:48, less than 1:49, less than 1:50, less than 1:41, less than 1:42, less than 1:43, less than 1:44, less than 1:45, less than 1:46, less than 1:47, less than 1:48, less than 1:49, less than 1:50, less than 1:51, less than 1:52, less than 1:53, less than 1:54, less than 1:55, less than 1:56, less than 1:57, less than 1:58, less than 1:59, less than 1:60, less than 1:61, less than 1:62, less than 1:63, less than 1:64, less than 1:65, less than 1:70, less than 1:75, less than 1:80, less than 1:85, less than 1:90, less than 1:95, less than 1:100, less than 1:125, less than 1:150, less than 1:175, less than 1:200, less than 1:225, less than 1:250, less than 1:275, less than 1:300, less than 1:325, less than 1:350, or less than 1:375).

Compositions and formulations can comprise a weight ratio of (a) penoxsulam or agriculturally acceptable salt thereof to (b) mefenacet or an agriculturally acceptable salt thereof from any of the minimum ratios described above to any of the maximum values described above. In some embodiments, the composition or formulation comprises a weight ratio of (a) penoxsulam or agriculturally acceptable salt thereof to (b) mefenacet or an agriculturally acceptable salt thereof that is sufficient to induce a synergistic herbicidal effect, and ranges from 1:400 to less than 1:30 (e.g., from 1:200 to less than 1:30, from 1:140 to less than 1:30, from 1:80 to less than 1:30, from 1:75 to less than 1:30, from 1:70 to less than 1:30, from 1:65 to less than 1:30, from 1:60 to less than 1:30, or from 1:56 to less than 1:30). In some embodiments, the weight ratio is from 1:56 to 1:7 or from 1:56 to 1:14.

Formulations

The present disclosure also relates to formulations of the compositions and methods disclosed herein. In some embodiments, the formulation can be in the form of a single package formulation including both (a) penoxsulam or an agriculturally acceptable salt thereof and (b) mefenacet or an agriculturally acceptable salt thereof. In some embodiments, the formulation can be in the form of a single package formulation including both (a) and (b) and further including at least one additive. In some embodiments, the formulation can be in the form of a two-package formulation, wherein one package contains (a) and optionally at least one additive while the other package contains (b) and optionally at least one additive. In some embodiments of the two-package formulation, the formulation including (a) and optionally at least one additive and the formulation including (b) and optionally at least one additive are mixed before application and then applied simultaneously. In some embodiments, the mixing is performed as a tank mix (i.e., the formulations are mixed immediately before or upon dilution with water). In some embodiments, the formulation including (a) and the formulation including (b) are not mixed but are applied sequentially (in succession), for example, immediately or within 1 hour, within 2 hours, within 4 hours, within 8 hours, within 16 hours, within 24 hours, within 2 days, or within 3 days of each other.

In some embodiments, the formulation of (a) and (b) is present in suspended, emulsified, or dissolved form. Exemplary formulations include, but are not limited to, aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, and materials for spreading or granules.

In some embodiments, (a) penoxsulam or an agriculturally acceptable salt thereof and/or (b) mefenacet or an agriculturally acceptable salt thereof is an aqueous solution that can be diluted before use. In some embodiments, (a) and/or (b) is provided as a high-strength formulation such as a concentrate. In some embodiments, the concentrate is stable and retains potency during storage and shipping. In some embodiments, the concentrate is a clear, homogeneous liquid that is stable at temperatures of 54° C. or greater. In some embodiments, the concentrate does not exhibit any precipitation of solids at temperatures of −10° C. or higher. In some embodiments, the concentrate does not exhibit separation, precipitation, or crystallization of any components at low temperatures. For example, the concentrate remains a clear solution at temperatures below 0° C. (e.g., below −5° C., below −10° C., below −15° C.). In some embodiments, the concentrate exhibits a viscosity of less than 50 centipoise (50 megapascals), even at temperatures as low as 5° C.

The compositions and methods disclosed herein can also be mixed with or applied with an additive. In some embodiments, the additive can be diluted in water or can be concentrated. In some embodiments, the additive is added sequentially. In some embodiments, the additive is added simultaneously. In some embodiments, the additive is premixed with the penoxsulam or agriculturally acceptable salt thereof. In some embodiments, the additive is premixed with the mefenacet or agriculturally acceptable salt thereof. In some embodiments, the additive is premixed with the penoxsulam or agriculturally acceptable salt thereof and the mefenacet or agriculturally acceptable salt thereof.

In some embodiments, the additive is an additional pesticide. Exemplary additional pesticides include, but are not limited to, 2,4-D, acetochlor, aclonifen, amicarbazone, 4-aminopicolinic acid based herbicides, such as those described in U.S. Pat. Nos. 7,314,849 and 7,432,227 to Balko, et al., amidosulfuron, aminocyclopyrachlor, aminopyralid, aminotriazole, ammonium thiocyanate, anilofos, asulam, azimsulfuron, atrazine, beflubutamid, benazolin, benfuresate, bensulfuron-methyl, bentazon-sodium, benzobicyclon, benzofenap, bifenox, bispyribac-sodium, bromobutide, bromacil, bromoxynil, butachlor, butafenacil, butralin, butroxydim, carbetamide, cafenstrole, carfentrazone, carfentrazone-ethyl, chlormequat, clopyralid, chlorsulfuron, chlortoluron, cinidon-ethyl, clethodim, clodinafop-propargyl, clomeprop, clomazone, cloransulam-methyl, cyanazine, cyclosulfamuron, cycloxydim, cyhalofop-butyl, daimuron, dicamba, dichlobenil, dichlorprop-P, diclofop-methyl, diclosulam, diflufenican, diflufenzopyr, dimefuron, dimethachlor, diquat, diuron, s-ethyl dipropyl-carbamothioate (EPTC), esprocarb, ethoxysulfuron, etobenzanid, fenoxaprop, fenoxaprop-ethyl, fenoxaprop-ethyl+isoxadifen-ethyl, fenoxaprop-P-ethyl, fenoxasulfone, fentrazamide, flazasulfuron, florasulam, fluazifop, fluazifop-P-butyl, flucarbazone, flucabazone-sodium, flucetosulfuron (LGC-42153), flufenacet, flumetsulam, flumioxazin, flupyrsulfuron, flurochloridone, fluroxypyr, fluroxypyr-meptyl, flurtamone, glufosinate, glufosinate-ammonium, glyphosate, halauxifen, halauxifen-methyl, halosulfuron-methyl, haloxyfop-methyl, haloxyfop-R-methyl, hexazinone, imazamethabenz, imazamox, imazapic, imazapyr, imazaquin, imazethapyr, imazosulfuron, indanofan, indaziflam, iodosulfuron, iodosulfuron-ethyl-sodium, ioxynil, ipfencarbazone, isoproturon, isoxaben, isoxaflutole, lactofen, linuron, MCPA, MCPB, mecoprop-P, mesosulfuron, mesosulfuron-ethyl sodium, mesotrione, metamifop, metazochlor, metazosulfuron, metosulam, metribuzin, metsulfuron, metsulfuron-methyl, molinate, MSMA, napropamide, napropamide-M, norfurazon, orthosulfamuron, oryzalin, oxadiargyl, oxadiazon, oxazichlomefone, oxyfluorfen, paraquat, pendimethalin, pentoxazone, pethoxamid, picloram, picolinafen, pinoxaden, pretilachlor, primisulfuron, profluazol, profoxydim, propanil, propaquizafop, propyrisulfuron, propoxycarbazone, propyzamide, prosulfocarb, prosulfuron, pyraclonil, pyraflufen-ethyl, pyrasulfotole, pyrazosulfuron-ethyl, pyrazolynate, pyribenzoxim (LGC-40863), pyributicarb, pyridate, pyriftalid, pyrimisulfan, pyroxsulam, pyroxasulfone, quinclorac, quinmerac, quizalofop-ethyl-D, quizalofop-P-ethyl, quizalofop-P-tefuryl, rimsulfuron, sethoxydim, simazine, sulfentrazone, sulfometuron, sulfosate, sulfosulfuron, tebuthiuron, tefuryltrione, tepraloxidim, terbacil, terbuthylazine, terbutryn, thenylchlor, thiazopyr, thifensulfuron, thifensulfuron-methyl, thiobencarb, topramezone, tralkoxydim, triafamone, triasulfuron, tribenuron, tribenuron-methyl, triafamone, triclopyr, and trifluralin, and agriculturally acceptable salts, choline salts, esters and mixtures thereof.

In certain embodiments, the additional pesticide includes cyhalofop-butyl, bensulfuron-methyl, bentazon-sodium, benzobicyclon, bromobutide, fenoxaprop-ethyl, halosulfuron-methyl, metamifop, metazosulfuron, metsulfuron-methyl, profoxydim, pyrazosulfuron-ethyl, triafamone, or combinations thereof.

In some embodiments, the penoxsulam or an agriculturally acceptable salt thereof is provided in a premixed formulation with an additional pesticide. In some embodiments, the penoxsulam or an agriculturally acceptable salt thereof is premixed with, cyhalofop-butyl, oxyfluorfen, triclopyr, or combinations thereof. Exemplary premixes of penoxsulam or an agriculturally acceptable salt or ester thereof and an additive that are or have been commercially available include, but are not limited to, CLINTON® (a premix incorporating cyhalofop-butyl by Dow AgroSciences LLC), REBELEX® (a premix incorporating cyhalofop-butyl by Dow AgroSciences LLC), RICER® (a premix incorporating cyhalofop-butyl by Dow AgroSciences LLC), TOPSHOT® (a premix incorporating cyhalofop-butyl by Dow AgroSciences LLC), PINDAR GT® (a premix incorporating oxyfluorfen by Dow AgroSciences LLC), and GRASP® XTRA (a premix incorporating triclopyr by Dow AgroSciences LLC).

In some embodiments, the mefenacet or an agriculturally acceptable salt thereof is provided in a premixed formulation with an additional pesticide. In some embodiments, the mefenacet or an agriculturally acceptable salt or ester thereof is premixed with bensulfuron-methyl, bromobutide, daimuron, MCPB, naproanilide, pyrazolynate, pyrazosulfuron-ethyl, simetryn, tefuryltrione, thiobencarb, or combinations thereof. Exemplary premixes of mefenacet or an agriculturally acceptable salt or ester thereof and an additive that are or have been commercially available include, but are not limited to, MANSOKUM® (a premix incorporating bensulfuron-methyl by Bayer CropScience), TIAN CAO LING® (a premix incorporating bensulfuron-methyl by Shanghai Agro-Chemical Industry Co., Ltd.), YI DA® (a premix incorporating bensulfuron-methyl by Nanjing Red Sun Co., Ltd.), ZARK® (a premix incorporating bensulfuron-methyl by DuPont), ZARK D® (a premix incorporating bensulfuron-methyl and daimuron by DuPont), WOLF ACE® (a premix incorporating bensulfuron-methyl and thiobencarb by Kumiai Chemical Industry Co., Ltd.), SIUZAN® (a premix incorporating bromobutide and naproanilide by Bayer CropScience), LEEDZON® (a premix incorporating bromobutide and pyrazolynate by Bayer CropScience), CHLOA SM® (a premix incorporating MCPB and simetryn by Bayer CropScience), ACT® (a premix incorporating pyrazosulfuron-ethyl by Bayer CropScience), and POSSIBLE® (a premix incorporating tefuryltrione by Bayer CropScience), In some embodiments, the additive includes an agriculturally acceptable adjuvant. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, safeners, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85%)+emulsifiers (15%)), nonylphenol ethoxylate, benzylcocoalkyldimethyl quaternary ammonium salt, blend of petroleum hydrocarbon, alkyl esters, organic acid, and anionic surfactant, $C_9$-$C_{11}$ alkylpolyglycoside, phosphate alcohol ethoxylate, natural primary alcohol ($C_{12}$-$C_{16}$) ethoxylate, di-sec-butylphenol EO-PO block copolymer, polysiloxane-methyl cap, nonylphenol ethoxylate+urea ammonium nitrate, emulsified methylated seed oil, tridecyl alcohol (synthetic) ethoxylate (8 EO), tallow amine ethoxylate (15 EO), and PEG(400) dioleate-99.

In some embodiments, the additive is a safener that is an organic compound leading to better crop plant compatibility when applied with a herbicide. In some embodiments, the safener itself is herbicidally active. In some, the safener acts as an antidote or antagonist in the crop plants and can reduce or prevent damage to the crop plants. Exemplary safeners include, but are not limited to, AD-67 (MON 4660), benoxacor, benthiocarb, brassinolide, cloquintocet (mexyl), cyometrinil, cyprosulfamide, daimuron, dichlormid, dicyclonon, dietholate, dimepiperate, disulfoton, fenchlorazole, fenchlorazole-ethyl, fenclorim, flurazole, fluxofenim, furilazole, harpin proteins, isoxadifen-ethyl, jiecaowan, jiecaoxi, mefenpyr, mefenpyr-diethyl, mephenate, naphthalic anhydride, 2,2,5-trimethyl-3-(dichloroacetyl)-1,3-oxazolidine, 4-(dichloroacetyl)-1-oxa-4-azaspiro[4.5]decane, oxabetrinil, R29148, and N-phenyl-sulfonylbenzoic acid amides, as well as agriculturally acceptable salts thereof and, provided they have a carboxyl group, their agriculturally acceptable derivatives. In some embodiments, the safener can be cloquintocet or an ester or salt thereof, such as cloquintocet (mexyl). For example, cloquintocet can be used to antagonize harmful effects of the compositions on rice and cereals.

Exemplary surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivates, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamine B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid or solid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like, vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like, esters of the above vegetable oils, esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, dibutyl adipate, di-octyl phthalate and the like, esters of mono, di and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof. Exemplary solid carriers include, but are not limited to, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, pyrophyllite clay, attapulgus clay, kieselguhr, calcium carbonate, bentonite clay, Fuller's earth, cottonseed hulls, wheat flour, soybean flour, pumice, wood flour, walnut shell flour, lignin, ammonium sulfate, ammonium phosphate, ammonium nitrate,ureas, cereal meal, tree bark meal, wood meal and nutshell meal, cellulose powders, and mixtures thereof.

In some embodiments, emulsions, pastes or oil dispersions, can be prepared by homogenizing (a) and (b) in water by means of wetting agent, tackifier, dispersant or emulsifier. In some embodiments, concentrates suitable for dilution with water are prepared, comprising (a), (b), a wetting agent, a tackifier, and a dispersant or emulsifier.

In some embodiments, powders or materials for spreading and dusts can be prepared by mixing or concomitant grinding of (a) and (b) and optionally a safener with a solid carrier.

In some embodiments, granules (e.g., coated granules, impregnated granules and homogeneous granules) can be prepared by binding the (a) and (b) to solid carriers.

The formulations disclosed herein can comprise a synergistic, herbicidally effective amount of (a) and (b). In some embodiments, the concentrations of (a) and (b) in the formulations can be varied. In some embodiments, the formulations comprise from 1% to 95% (e.g., from 5% to 95%, from 10% to 80%, from 20% to 70%, from 30% to 50%) by total weight of (a) and (b). In some embodiments, (a) and (b), independently, can be employed in a purity of from 90% to 100% (e.g., from 95% to 100%) according to nuclear magnetic resonance (NMR) spectrometry. In some embodiments, the concentrations of (a), (b), and additional pesticides in the formulations can be varied. In some embodiments, the formulations comprise from 1% to 95% (e.g., from 5% to 95%, from 10% to 80%, from 20% to 70%, from 30% to 50%) by total weight of (a), (b), and additional pesticides. In some embodiments, (a), (b), and additional pesticides, independently, can be employed in a purity of from 90% to 100% (e.g., from 95% to 100%) according to NMR spectrometry.

Methods of Application

The compositions disclosed herein can be applied in any known technique for applying herbicides. Exemplary application techniques include, but are not limited to, spraying, atomizing, dusting, spreading, or direct application into water (in-water). The method of application can vary depending on the intended purpose. In some embodiments, the method of application can be chosen to ensure the finest possible distribution of the compositions disclosed herein.

The compositions disclosed herein can be applied pre-emergence (before the emergence of undesirable vegetation) or post-emergence (i.e., during and/or after emergence of the undesirable vegetation). The composition can be applied, for example, to the vegetation as an in-water application to a flooded rice field.

When the compositions are used in crops, the compositions can be applied after seeding and before or after the emergence of the crop plants. In some embodiments, the compositions disclosed herein show good crop tolerance even when the crop has already emerged, and can be applied during or after the emergence of the crop plants. In some embodiments, when the compositions are used in crops, the compositions can be applied before seeding of the crop plants.

In some embodiments, the compositions disclosed herein are applied to vegetation or an area adjacent the vegetation, or applied to soil, or applied to/into water, for example to/into flooded rice fields, to prevent the emergence or growth of vegetation by spraying (e.g., foliar spraying or spraying into the water of a flooded rice field). In some embodiments, the spraying techniques use, for example, water as carrier and spray liquor rates of from 10 liters per hectare (L/ha) to 2000 L/ha (e.g., from 50 L/ha to 1000 L/ha, or from 100 to 500 L/ha). In some embodiments, the compositions disclosed herein are applied by the low-volume or the ultra-low-volume method, wherein the application is in the form of micro granules. In some embodiments, the compositions disclosed herein can be applied as dry formulations (e.g., granules, WDGs, etc.) into water.

In some embodiments, herbicidal activity is exhibited by the compounds of the synergistic mixture when they are applied directly to the plant or to the locus of the plant at any stage of growth or before planting or emergence. The effect observed can depend upon the type of undesirable vegetation to be controlled, the stage of growth of the undesirable vegetation, the application parameters of dilution and spray drop size, the particle size of solid components, the environmental conditions at the time of use, the specific compound employed, the specific adjuvants and carriers employed, the soil type, and the like, as well as the amount of chemical applied. In some embodiments, these and other factors can be adjusted to promote non-selective or selective herbicidal action.

The compositions and methods disclosed herein can be used to control undesired vegetation in a variety of crop and non-crop applications. In some embodiments, the compositions and methods disclosed herein can be used for controlling undesired vegetation in rice (e.g., in flooded seeded rice, in flooded transplanted rice, or in rice seedbeds prior to planting rice seeds or rice transplants).

The compositions and methods disclosed herein can also be used in crop plants that are resistant to, for instance, herbicides, pathogens, and/or insects. In some embodiments, the compositions and methods disclosed herein can be used in crop plants that are resistant to one or more herbicides because of genetic engineering or breeding. In some embodiments, the compositions and methods disclosed herein can be used in crop plants that are resistant to one or more pathogens such as plant pathogenous fungi owing to genetic engineering or breeding. In some embodiments, the compositions and methods disclosed herein can be used in crop plants that are resistant to attack by insects owing to genetic engineering or breeding.

In some embodiments, the crop is rice that is resistant to synthetic auxins, or rice that, owing to introduction of the gene for *Bacillus thuringiensis* (or Bt) toxin by genetic modification, is resistant to attack by certain insects. In some embodiments, the compositions and methods described herein also can be used in conjunction with glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil to control vegetation in rice that is tolerant to glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, bromoxynil, or combinations thereof. In some embodiments, the undesirable vegetation is controlled in glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil tolerant rice possessing multiple or stacked traits conferring tolerance to multiple chemistries and/or multiple modes of action. The combination of (a), (b), and a complementary herbicide or salt or ester thereof can be used in combination with herbicides that are selective for the rice being treated and which complement the spectrum of weeds controlled by these compounds at the application rate employed.

The herbicidal compositions prepared disclosed herein are effective against a variety of types of undesirable vegetation, including undesirable vegetation that frequently poses a challenge in rice fields by competing for water, sunlight and nutrients. In some embodiments, the compositions disclosed herein can be used for controlling undesirable vegetation including grasses, broadleaf weeds, sedge weeds, and combinations thereof. For example, the compositions and methods provided herein can be used to control undesirable vegetation including, but not limited to, undesirable vegetation of the weed genera *Echinochloa, Eleocharis, Lindernia,* and *Sagittaria*. Examples of grass weeds controlled by the compositions and methods provided herein include, but are not limited to, *Brachiaria platyphylla* (Broadleaf signalgrass, BRAPP), *Echinochloa crus-galli* (Barnyardgrass, ECHCG), *Echinochloa colonum* (Junglerice, ECHCO), *Echinochloa oryzoides* (Early watergrass, ECHOR), *Leptochloa chinensis* (Chinese sprangletop, LEFCH), *Leptochloa fascicularis* (Bearded sprangletop, LEFFA), *Ischaemum rugosum* Salisb. (Saramollagrass, ISCRU), *Leptochloa panicoides* (Amazon sprangletop, LEFPA), and combinations thereof. Examples of sedge weeds controlled by the compositions and methods provided herein include, but are not limited to, *Cyperus difformis* (Smallflower flatsedge, CYPDI), *Cyperus esculentus* (Yellow nutsedge, CYPES), *Cyperus iria* (Rice flatsedge, CYPIR), *Cyperus rotundus* (Purple nutsedge, CYPRO), *Fimbristylis miliacea* (Globe fringerush, FIMMI), *Schoenoplectus juncoides* (Roxb.) Palla (Japanese bulrush, SCPJU), *Schoenoplectus mucronatus* (Ricefield bulrush, SCPMU), and combinations thereof. Examples of broadleaf weeds controlled by the compositions and methods provided herein include, but are not limited to, *Aeschynomene* species (Jointvetch, AESSS), *Alternanthera philoxeroides* (Alligatorweed, ALRPH), *Alisma plantago-aquatica* (Common waterplantain, ALSPA), *Amaranthus* species (Pigweeds, AMASS), *Ammannia coccinea* (Purple ammannia, AMMCO), *Eclipta alba* (American false daisy, ECLAL), *Heteranthera limosa* (Ducksalad, HETLI), *Monochoria vaginalis* (Monochoria, MOOVA), *Sagittaria* species (Arrowhead, SAGMO), *Sesbania exaltata* (Hemp sesbania, SEBEX), *Sphenoclea zeylanica* (Gooseweed, SPDZE), and combinations thereof. Additional examples of weeds controlled by the compositions and methods provided herein include, but are not limited to *Echinochloa oryzicola* (Late Watergrass, ECHPH), *Lindernia dubia* (low false pimpernel, LIDDU), *Heteranthera reniformis* (round-leaf mud plantain, HETRE), *Murdannia nudiflora* (doveweed, MUDNU), *Monochoria korsakowii* (mizuaoi, MOOKO), *Alternanthera philoxeroides* (alligator weed, ALRPH), *Schoenoplectus maritimus* (puma grass, SCPMA), and combinations thereof.

In certain cases, the undesirable vegetation that can be controlled by the combination of (a) and (b) is selected from *Echinochloa crus-galli* (barnyard grass, ECHCG), *Eleocharis kuroguwai* (kuro-guwai, ELOKU), *Lindernia procumbens* (common false pimpernel, LIDPY), *Sagittaria pygmaea* (dwarf arrowhead, SAGPY), and combinations thereof.

By way of non-limiting illustration, examples of certain embodiments of the present disclosure are given below.

EXAMPLES

Evaluation of Application of Penoxsulam and Mefenacet for Synergistic Weed Control Field trials were conducted in Japan with applications made in the area of naturally occurring weed populations. All treatments were applied using a randomized complete block trial design, with 3 replications per treatment. Plot size was 2 meters (m)×2 m (width×length), with each plot being a separate entity and flooded with water. Rice was transplanted into the plots, and the rice crop was maintained as a normal commercial crop with appropriate fertilizer and maintenance treatments as needed. Rice size at application varied from 4 leaf to 2 tiller stage, and weeds were 1 to 5 leaf stage. All plots were maintained flooded to 3 to 6 centimeter (cm) depth and treatments were applied by hand directly into the flooded plots containing the rice and weeds.

Treatments consisted of penoxsulam and mefenacet, applied alone or in combination. Penoxsulam was applied as a granule formulation (3.5 grams of active ingredient per kilogram (g ai/kg) granule (GR)) applied directly into the flooded plots, or as a liquid formulation (31 grams of active ingredient per liter (g ai/L) emulsifiable concentrate (EC)) mixed in 1 liter (L) of solution and applied into the flooded plots. Mefenacet, as the commercial product HINOCHLOA® containing 40 g ai/kg GR, was applied directly into the flooded plots.

The treated plots and control plots were rated blind at various intervals after application. Ratings were based on a scale of 0-100%, as discussed above, wherein 0% indicates complete growth of the undesired vegetation and 100% indicates complete prevention of the undesired vegetation.

Colby's equation was used to determine the herbicidal effects expected from the mixtures, as described above. The results were measured at the evaluation intervals provided in Table 1 after the application of the compositions (penoxsulam and mefenacet, applied alone or in combination). The trials exhibited unexpected synergy, and those results were found statistically significant under the p-value test. The herbicide tank mix combinations tested, application rates and ratios employed, plant species tested, and results are included in Table 1 below.

TABLE 1

Synergistic % Visual Weed Control from applications of Penoxsulam + Mefenacet for the control of undesirable vegetation in rice.

| | | Penoxsulam | | Mefenacet | | Combination | |
|---|---|---|---|---|---|---|---|
| Weed Bayer | Evaluation Interval | g ai/ha | Mean % weed control | g ai/ha | Mean % weed control | Measured mean % weed control | Colby predicted mean % weed control |
| ECHCG | 42 days | 18 | 81 | 750 | 40 | 98 | 89 |
| ELOKU | 44 days | 70 | 81 | 1000 | 23 | 99 | 85 |
| ELOKU | 52 days | 18 | 34 | 1000 | 20 | 60 | 48 |
| ELOKU | 52 days | 70 | 71 | 1000 | 20 | 94 | 76 |
| ELOKU | 52 days | 35 | 62 | 750 | 33 | 85 | 75 |
| ELOKU | 61 days | 70 | 61 | 1000 | 0 | 85 | 61 |
| ELOKU | 61 days | 35 | 49 | 1000 | 0 | 67 | 49 |
| ELOKU | 34 days | 18 | 62 | 1000 | 0 | 79 | 62 |
| ELOKU | 34 days | 18 | 62 | 500 | 0 | 84 | 62 |
| ELOKU | 34 days | 18 | 62 | 750 | 0 | 74 | 62 |
| LIDPY | 23 days | 18 | 87 | 500 | 0 | 99 | 87 |
| LIDPY | 23 days | 18 | 87 | 750 | 27 | 100 | 91 |
| LIDPY | 42 days | 18 | 83 | 500 | 0 | 90 | 83 |
| LIDPY | 18 days | 18 | 73 | 1000 | 57 | 100 | 88 |
| LIDPY | 18 days | 18 | 73 | 500 | 43 | 100 | 83 |
| LIDPY | 18 days | 18 | 73 | 750 | 50 | 100 | 86 |
| LIDPY | 24 days | 18 | 86 | 500 | 0 | 100 | 86 |
| SAGPY | 44 days | 35 | 82 | 500 | 0 | 100 | 82 |
| SAGPY | 44 days | 35 | 82 | 750 | 0 | 100 | 82 |

As shown above, the treatments demonstrated synergistic weed control, with higher measured weed control than would be predicted by the Colby equation.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method of controlling undesirable vegetation in rice which comprises applying to the undesirable vegetation or an area adjacent the vegetation, or applying to soil or water to control the emergence or growth of the undesirable vegetation, a synergistically herbicidal effective amount of (a) penoxsulam, or an agriculturally acceptable salt thereof, and (b) mefenacet, or an agriculturally acceptable salt thereof,
   wherein (a) and (b) are applied in a weight ratio of (a) to (b) from 1:56 to 1:42, and
   wherein the undesirable vegetation includes barnyard grass, kuro-guwai, common false pimpernel, dwarf arrowhead, or combinations thereof.

2. The method of claim 1, wherein (a) and (b) are applied simultaneously.

3. The method of claim 1, wherein (a) and (b) are applied to water to control the emergence or growth of the undesirable vegetation.

4. The method of claim 1, further comprising applying an additional pesticide.

5. The method of claim 4, wherein the additional pesticide includes one or more pesticides selected from the group consisting of cyhalofop-butyl, bensulfuron-methyl, bentazon-sodium, benzobicyclon, bromobutide, fenoxaprop-ethyl, halosulfuron-methyl, metamifop, metazosulfuron, metsulfuron-methyl, profoxydim, pyrazosulfuron-ethyl, triafamone, and combinations thereof.

6. The method of claim 1, wherein the undesirable vegetation is controlled in flooded rice.

7. The method of claim 1, wherein (a) is applied in an amount of from 5-75 g ai/ha.

8. The method of claim 1, wherein (b) is applied in an amount of from 250-2000 g ai/ha.

9. The method of claim 1 wherein the undesirable vegetation includes kuro-guwai, common false pimpernel, dwarf arrowhead, or combinations thereof.

* * * * *